United States Patent [19]

Stanker et al.

[11] Patent Number: 5,108,900
[45] Date of Patent: Apr. 28, 1992

[54] MONOCLONAL ANTIBODIES TO SYNTHETIC PYRETHROIDS AND METHOD FOR DETECTING THE SAME

[75] Inventors: Larry H. Stanker, Livermore; Martin Vanderlaan, Danville; Bruce E. Watkins, Livermore, all of Calif.; Jeanette M. Van Emon, Henderson, Nev.; Carolyn L. Bigbee, Livermore, Calif.

[73] Assignee: Regents of the University of California, Oakland, Calif.

[21] Appl. No.: 319,102

[22] Filed: Mar. 6, 1989

[51] Int. Cl.⁵ .................... G01N 33/543; C12N 5/20; C07K 15/28
[52] U.S. Cl. .................... 435/7.93; 435/7.5; 435/172.2; 435/240.27; 436/548; 436/815; 436/822; 530/388.9
[58] Field of Search .................... 435/7.5, 7.93, 172.2, 435/240.27; 436/548, 815, 822; 530/387

[56] References Cited

FOREIGN PATENT DOCUMENTS 0235000 9/1987 European Pat. Off. .

OTHER PUBLICATIONS

Tijssen, P., *Practice and Theory of Enzyme Immunoassays*, vol. 15, Burdon et al., ed., Elsevier, New York, pp. 21–31, 1985.
Braun et al., *J. Assoc. Off. Anal. Chem.* 68(3) 685–689, 1982.
Vanderlaan et al., "Monoclonal Antibodies for the Detection of Trace Chemicals", *Pesticide Science and Biotechnology*, (1987), pp. 597–602.
Vanderlaan et al., "Environmental Monitoring by Immunoassay", *Environ. Sci. Technol.*, vol. 22, No. 3, 1988, pp. 247–254.

*Primary Examiner*—Mary E. Ceperley
*Attorney, Agent, or Firm*—Nora A. Hackett

[57] ABSTRACT

Methods are described for making specific monoclonal antibodies which may be used in a sensitive immunoassay for detection of synthetic pyrethroids in foods and environmental samples. Appropriate sample preparation and enzyme amplification of the immunoassay for this widely-used class of pesticides permits detection at low levels in laboratory and field tested samples.

4 Claims, 6 Drawing Sheets

MONOCLONAL ANTIBODIES TO SYNTHETIC PYRETHROIDS AND METHOD FOR DETECTING THE SAME

The U.S. Government has rights in this invention pursuant to Contract No. W-7405-ENG-48 between The Regents of The University of California and the U.S. Department of Energy.

The subject invention is related generally to monoclonal antibodies and more specifically to monoclonal antibodies reactive with synthetic pyrethroids found in foods and environmental samples.

IDENTIFICATION OF TERMS

Abbreviations or definitions used in the disclosure herein are as follows:

cELISA, competition enzyme-linked immunosorbent assay;
BSA, bovine serum albumin;
KLH, keyhole limpet hemocyanin;
GC/EC, gas chromatography/electron capture;
hapten, a small molecule which carries an antigenic determinant, but is not immunogenic until it is chemically coupled to a larger protein carrier. The hapten-carrier complex then stimulates an immune competent cell to form antibodies to the hapten and the complex;
HPLC, high pressure liquid chromatography;
Soxhlet apparatus, a solvent extraction still in which condensed solvent vapors repeatedly pass through a sample to extract organic materials;
synthetic pyrethroids, a large group of non-naturally occuring compounds, related to pyrethrum, a mixture of esters of chrysanthemic and pyrethric acids, which are used as insecticides, including the widely used compounds, permethrin, cypermethrin and deltamethrin, and less commonly used compounds, phenothrin, fenpropathrin, flucythranate, fenvalerate and tetramethrin;
cypermethrin, alpha-cyano-3-phenoxybenzyl cis, trans-3-(2,2-dichlorovinyl)-2,2-dimethylcyclopropanecarboxylate;
fenpropathrin, alpha-cyano-3-phenoxybenzyl-2,2,3,3-tetramethylcyclopropanecarboxylate;
deltamethrin, −/+alpha-cyano-3-phenoxybenzyl-(+/−)-cis,trans-3-(2,2-dibromovinyl)-2,2-dimethylcyclopropanecarboxylate;
fenvalerate, cyano(3-phenoxyphenyl)methyl 4-chloroalpha-(1-methylethyl)benzeneacetate;
flucythranate, cyano(3-phenoxyphenyl)methyl(S)-4-(difluoromethoxy)-alpha-(1-methylethyl) benzeneacetate;
permethrin, 3-phenoxybenzyl (IRS),cis,trans-3(2,2-dichlorovinyl)-2,2-dimethylcyclopropanecarboxylate;
phenothrin, 3-phenoxybenzyl(1RS)cis,transchrysanthemate;
tetramethrin, N-(3,4,5,6-tetrahydrophthalimino) methyl (dl)-cis,trans-chrysanthemate

BACKGROUND OF THE INVENTION

Monoclonal antibodies have considerable usefulness as diagnostic and therapeutic agents in clinical, commercial and research applications. Refinements of the general technique for hybridoma production developed by Kohler and Milstein in 1975 (*Nature* 256: 495–497) make it possible to produce large quantities of monoclonal antibodies which are able to recognize specific antigenic determinants.

While development of antibodies reactive to protein antigenic sites is known and repeatable, fabrication of monoclonal antibodies reactive to small organic chemicals, such as carcinogens, pesticides, toxic chemicals and DNA adducts is less straight-forward. Production of antibodies to small organic molecules may sometimes be achieved by first linking a small molecule, which is termed a hapten, to a carrier protein, and the immune reactive cells may respond to an antigenic determinant site of this complex. Initial chemical treatment of the small molecule hapten, may be required in order for it to be conjugated to an immunoreactive carrier protein. The immunoreactive cells are induced to form antibodies which have recognition sites to various reactive sites located (1) on the hapten molecule, (2) the carrier protein, (3) the hapten carrier-protein complex, or (4) any combination of the hapten, the linkage chemistry and the carrier protein. The specific reactive site is not known and is unpredictable. The site and chemistry of the hapten conjugation to the carrier protein may influence the specificity of the antibodies produced.

Antibodies with specific binding to reactive sites on small organic molecules are sensitive indicators, which may be used to distinguish chemical isomers (Stanker et al, *Toxicology* 45: 229–243 1987). With small haptens, the greatest antibody specificity for a reactive group appears to occur when that reactive group is most distant from the site of the linkage binding to the carrier protein. This work with synthetic pyrethroids demonstrates that conjugation of the hapten antigenic site as far as possible from the 3-phenoxybenzyl group favors the production of antibodies which preferentially recognize the phenoxybenzyl group. The phenoxybenzyl group is shared by many synthetic pyrethroids, and thus antibodies induced against one of the reactive groups of synthetic pyrethroids may recognize several members of the class of synthetic pyrethroids which carry that reactive group.

Synthetic pyrethroids are a large group of insecticides which are widely used in the United States and other countries. The synthetic pyrethroids most commonly used in the United States are permethrin, cypermethrin and deltamethrin; other synthetic pyrethroids include phenothrin, fenpropathrin, flucythranate, fenvalerate, and tetramethrin, among other compounds. The three most commonly used compounds contain both a phenoxybenzyl and a cyclopropane moiety. The other less used synthetic pyrethroids contain at least one of these groups, or a phenoxyphenyl moiety in place of the phenoxybenzyl moiety. In 1982, synthetic pyrethroids represented as much as 30% of the world insecticide market.

The synthetic pyrethroids in use differ widely in their chemical structure, toxicity and photostability. Historically, the agricultural use of synthetic pyrethroids, such as allethrin and bioallethrin, was limited due to the unstable character of those compounds in the air and water. However, recently developed synthetic pyrethroids such as permethrin, cypermethrin and deltamethrin are more stable and thus have greater agricultural utility. These compounds are widely used for insect control in food processing plants because they display low mammalian toxicity. Widespread use of these more stable compounds, however, has led to concern about the possiblity that pesticide residues might remain in foodstuffs and the environment. Both cypermethrin and permethrin have been listed as potentially oncogenic pesticides by the U.S. Environmental Protection Agency. (See Regulating Pesticides in Food: The Delaney Paradox, National Research Council Board on Agriculture, National Academy Press, Washington, D.C., 1987.)

Residue limits in meats and fats have been established in the United States for permethrin, cypermethrin and deltamethrin. Residue limits for many pyrethroids have been set by the Food and Agricultural Organization and the World Health Organization. However, the lack of convenient, rapid detection systems has hampered environmental identification and quantification of pyrethroids. Conventional analysis involves multi-step sample clean-up procedures followed by gas chromatography, and due to thermal instabilities, detection is limited to electron capture (GC/EC). Analysis by high-pressure liquid chromatography (HPLC) has also been described, but this separation technique cannot adequately resolve the various synthetic pyrethroids. Detection is also a problem with HPLC analysis. The complexity of standard chemical extraction and purification of compounds of such low incidence has engendered a need for other means by which to identify, rapidly and specifically, and to quantify these materials. Specific characterization of the presence and concentration of these compounds by assay with anti-pyrethroid monoclonal antibodies would permit, rapid, automatable analysis of these materials in foods and environmental samples.

SUMMARY OF THE INVENTION

Accordingly, it is an object of the present invention to provide monoclonal antibodies and the hybridomas that produce such monoclonal antibodies which will react specifically and sensitively with synthetic pyrethroids, particularly those antibodies with a high degree of specificity for a class of synthetic pyrethroids which possess the phenoxybenzyl or cyclopropane functionalities, and more particularly those antibodies with a high degree of specificity for a class of synthetic pyrethroids which possess the phenoxybenzyl and cyclopropane functionalities.

Another object is to provide a method for production of monoclonal antibodies which identify synthetic pyrethroids, preferably those with the phenoxybenzyl or cyclopropane moities, more preferably those with the phenoxybenzyl and cyclopropane moieties, and including production of a monoester of cyclopropanedicarboxylic acid hapten of phenothrin which will elicit formation of these antibodies.

A further object is to provide a method for the specific and sensitive detection and separation of synthetic pyrethroids from samples, particularly a class of synthetic pyrethroids which possess the phenoxybenzyl or cyclopropane functionalities, and more particularly a class of synthetic pyrethroids which possess the phenoxybenzyl and cyclopropane functionalities, by binding to specific monoclonal antibodies.

Another object is to provide a method for the detection of synthetic pyrethroids, particularly those with phenoxybenzyl or cyclopropane functionalities, and more particularly those with the phenoxybenzyl and cyclopropane functionalities, in environmental and food samples. A kit format of the detection system may be used for field analysis of surface wiped or extracted samples.

Additional objects, advantages and novel features of the invention will be set forth in part in the description which follows, and in part will become apparent to those skilled in the art upon examination of the following and the accompanying drawings and their descriptions which form part of the disclosure, or may be learned by practice of the invention. The objects and advantages of the invention may be realized and attained by means of the instrumentalities and combinations particularly pointed out in the appended claims.

To achieve the forgoing and other objects and in accordance with the purpose of the present invention as embodied and broadly described herein, the subject invention is directed to the monoclonal antibodies and the hybridomas which produce them which are specifically reactive to the synthetic pyrethroids which have a phenoxybenzyl or a cyclopropane group, and more specifically, to synthetic pyrethroids which have both a phenoxybenzyl group and a cyclopropane ring. Such compounds include, but are not limited to those shown on Table I, and derivatives thereof. The present invention also provides a method for the production and use of monoclonal antibodies reactive with the antigenic determinants on compounds selected from the group consisting of the synthetic pyrethroids which have a phenoxybenzyl or a cyclopropane moiety, or more preferably to a phenoxybenzyl and a cyclopropane moiety, and the hybrid cell lines which are capable of continuously producing these antibodies.

The method for the production of monoclonal antibodies to synthetic pyrethroids in accordance with the subject invention is adapted from the general method of Kohler and Milstein (1975) which is herein incorporated by reference. The production of pyrethroid-specific antibodies comprises immunizing a suitable animal with an antigen selected from the group consisting of synthetic pyrethroids, a monoester of cyclopropanedicarboxylic acid hapten of phenothrin, and immunogenic carrier protein conjugates of these compounds; obtaining from the animal immunosensitized cells, capable of producing antibodies to the antigen of choice; fusing the immunosensitized cells with immortally reproducing cells of the same species or of another animal species; culturing the hybrid cells in a suitable host or in a culture medium; isolating clones of hybrid cells, referred to as hybridomas, which continuously produce specific antibodies which react with the sensitizing antigen; selecting hybridomas which produce monoclonal antibodies of desired reactivity; producing these antibodies in culture medium or in a host; harvesting the antibodies from the culture medium or from the host used for growing the cells; and purifying the monoclonal antibodies, if desired.

According to a further aspect of the present invention, the cell lines developed in accordance with the instant invention are capable of producing highly specific monoclonal antibodies which may be used to distinguish the presence of synthetic pyrethroids in foods and environmental samples. These antibodies are contemplated to be useful for the sensitive detection of synthetic pyrethroids in tissue and surface samples. More specifically, the subject method of use provides for rapid, automatable screening of samples for synthetic pyrethroid compounds, with the use of synthetic pyrethroid specific monoclonal antibodies. The monoclonal antibodies produced are capable of recognizing synthetic pyrethroids, especially those with the functional groups, phenoxybenzyl or cyclopropane, and more especially, those with phenoxybenzyl and cyclopropane functional groups. The disclosed method may be used for identification and quantification of synthetic pyrethroid materials found in environmental samples and common foods. A kit format of the diagnostic method may be used for field testing of environmental surface wipe samples.

The synthetic pyrethroid-specific antibodies produced according to the present method may be used as attachment agents in an affinity column for the concentration and purification of synthetic pyrethroids. The antibodies produced also have application as detection agents for the indentification and quantification of synthetic pyrethroids following extraction. The extraction procedure for food or environmental samples assayed by specific monoclonal antibody assay may also be used when samples are assayed by GC/EC.

DETAILED DESCRIPTION OF THE INVENTION

Figure 1:
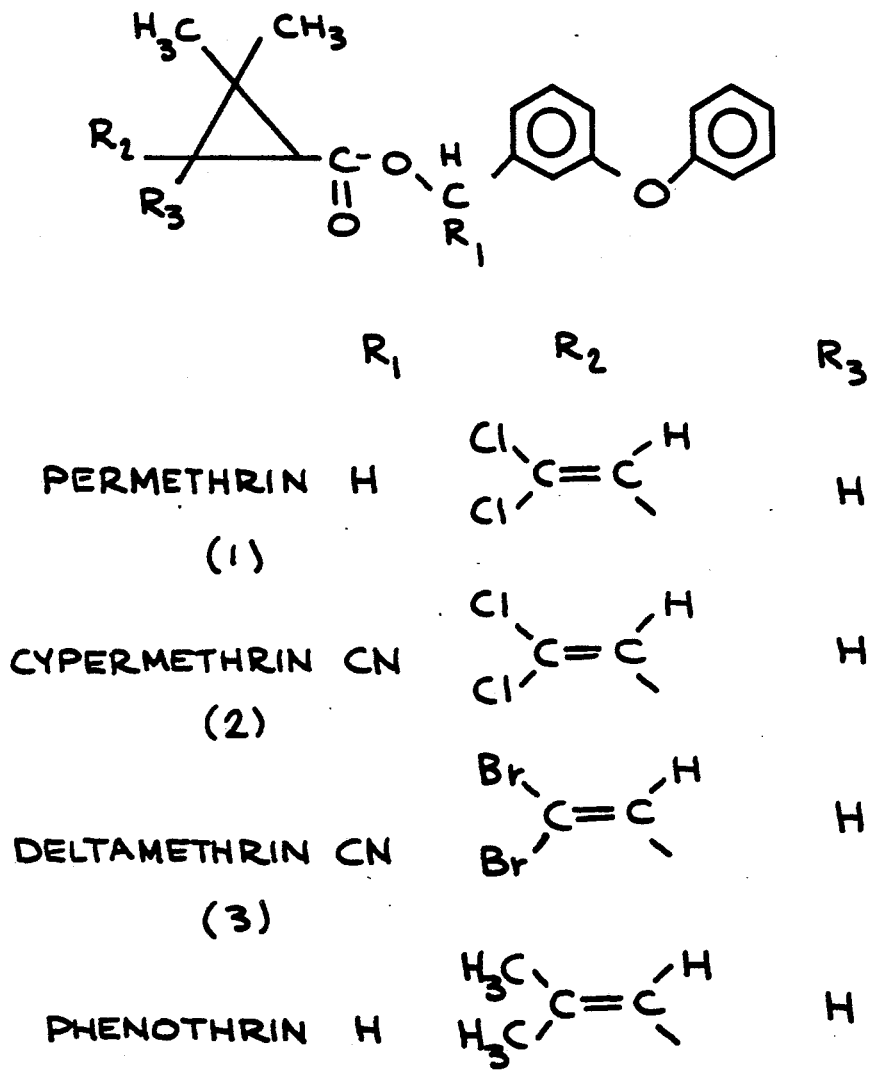
FIG. 1 shows the general chemical structure of synthetic pyrethroids specifically outlining the structures for permethrin (1), cypermethrin (2), deltamethrin (3) and phenothrin.

The subject invention is directed to a group of monoclonal antibodies, and the hybridomas which continuously produce them, which react specifically to the described group of synthetic pyrethroids, which contain the phenoxybenzyl or the cyclopropane functionalities, and more preferably to those which react with synthetic pyrethroids which contain both phenoxybenzyl and cyclopropane groups. The present invention also provides a method for the production of monoclonal antibodies reactive to synthetic pyrethroids with phenoxybenzyl or cyclopropane groups, more preferably to those reacting with synthetic pyrethroids with both a phenoxybenzyl and cyclopropane groups.

Techniques for the immunization of laboratory animals with synthetic peptides, which are analogs of protein fragments, and identification of specific protein epitopes, which are immunologically recognized features of a protein, as represented by antibody-inducing synthetic peptides, are known to those skilled in the art. However, when the antigen compounds are short peptide fragments or small nonproteinaceous molecules, injection of these compounds may fail to produce an adequate immune reaction in a test subject. Modified small molecules, termed haptens, may be conjugated to a known immunogen or to a carrier protein which is a known immunogen. By linkage into a small molecule-protein conjugate, the hapten may be rendered immunogenic. Antibodies produced in response to this immunogenic conjugate will sometimes recognize the small molecule apart from the carrier protein. Carrier proteins may be selected from any of a group of proteins which are immunogenic. Suitable carrier proteins include but are not limited to keyhole limpet hemocyanin (KLH), serum albumins, including bovine serum albumin (BSA), globulins including thyroglobulins and the like. Keyhole limpet hemocyanin (KLH) and bovine serum albumin (BSA) are conveniently employed in the subject invention.

Synthetic pyrethroids are small organic molecules, and in an effort to render such a molecule immunogenic, it was necessary to conjugate such molecules to carrier protein. Various modifications of synthetic pyrethroids can be made to achieve this purpose. For example, permethrin does not have functional groups through which it could be conjugated to a carrier protein, so it was necessary to synthesize an analog hapten, the monoester of cyclopropanedicarboxylic acid of phenothrin, for this purpose. Antibodies selected for their binding to the analog hapten of permethrin were also similarly responsive to the related pyrethroid compounds, permethrin and phenothrin, as well as the synthesized hapten, but were not responsive to the carrier protein alone.

The method for the production of monoclonal antibodies which are capable of distinguishing the presence of synthetic pyrethroids with the phenoxybenzyl or cyclopropane functionality, and more preferably of distinguishing presence of synthetic pyrethroids with the phenoxybenzyl and cyclopropane functionalities in accordance with the subject invention, comprises immunizing a suitable animal, preferably mice, rats, hamsters, rabbits, goats, sheep, cows and horses, still more preferably mice, with an antigen selected from the group consisting of the described synthetic pyrethroids with the phenoxybenzyl or cyclopropane functionality and a monoester of cyclopropanedicarboxylic acid hapten of phenothrin, which has been conjugated to an immunogenic carrier protein. Repeated administration of the antigen is made in a suitable amount, preferably between about 10 μg to about 200 μg, with about 100 μg (i.p.) per animal, per administration of pyrethroid carrier protein conjugate being especially preferred.

The antigen may be mixed with complete Freund's adjuvant, preferably in a 1:1 mixture, and administered at intervals of about two weeks for several, preferably three immunizations. Immunosensitized spleen cells or lymphocytes, preferably sensitized spleen cells which are now capable of producing antibodies to the antigen of choice are removed from the animal. The sensitized spleen cells or lymphocytes are fused with immortally reproducing cells, preferably myeloma cells of the first species or of another animal species to produce hybrid cells. The hybrid cells are cultured in a suitable host or in a culture medium. The clones of hybrid cells, known as hybridomas, which continuously produce or secrete specific antibodies to an antigen of the aforenamed group are isolated. Hybridomas which produce monoclonal antibodies that distinguish the presence of synthetic pyrethroids are selected, quantities of these monoclonal antibodies are generated, antibodies from the culture medium or from the host used for growing the cells are harvested, the monoclonal antibodies isolated and purified, if preferred, and monoclonal antibodies so produced are used to assay samples for the presence of synthetic pyrethroids. The hybridomas may be propagated in a suitable host animal or grown in a suitable culture or carrier medium. Host animals include but are not limited to mice, rats, hamsters, guinea pigs, rabbits, goats, sheep, cows and horses, and the like. Suitable culture media include, but are not limited to, ascites fluid and hybridoma supernatant, other than the one of the culture media specified above.

According to a further aspect of the present invention, in accordance with its objects and purposes, the hybridoma cell lines, designated as Py-1, Py-3, and Py-4, were developed. The clones of said cell lines are capable of producing monoclonal antibodies of high specificity to distinguish the presence of the described synthetic pyrethroids with the phenoxybenzyl or cyclopropane functionalities, more preferably to distinguish the presence of the described synthetic pyrethroids with the phenoxybenzyl or cyclopropane functionalities. The antibodies are given the same name as the cell line from which they are derived. These cell lines are deposited with the American Type Culture Collection (ATCC), 12301 Parklawn Drive, Rockville, Md. 20852 USA, and have been accorded Accession Numbers as follows: Py-1, ATCC No. HB 9996; Py-3, ATCC No. HB 9997 and Py-4, ATCC No. HB 9998.

These deposits were made pursuant to a contract between the ATCC and the assignee of this patent application. The contract with the ATCC provides for permanent availability of said strains and progeny thereof to the public upon issuance of a U.S. patent related to this application describing and identifying the deposit or upon the publication or laying open to the public of any U.S. or foreign patent application, whichever comes first and for the availability of these strains and the progeny thereof to one determined by the U.S. Commissioner of Patents and Trademarks to be entitled thereto according to 35 USC 122 and the Commissioner's rules pursuant thereto (including 37 CFR 1.14 with particular reference to 886 OG 638). The assignee of the present application has agreed that if the strains on deposit should die or be lost or destroyed when cultivated under suitable conditions, it will be promptly replaced upon notification with a viable culture of the same strain.

The depository, under the terms of the Budapest Treaty assures that said cultures deposited will be maintained in a viable and uncontaminated condition for a period of at least five years after the most recent request for the furnishing of a sample of a deposited hybridoma cell line was received by the ATCC and, in any case, for a period of at least 30 years after the date of the deposit.

Availability of the deposited strains is not to be construed as a license to practice the invention in contravention of the rights granted under the authority of any government in accordance with it's patent laws.

Also, the present invention is not to be considered limited in scope by the strains deposited, since the deposited embodiments are intended only to be illustrative of particular aspects of the invention. Any hybridoma cell lines which are functionally equivalent to these deposited are considered to be within the scope of this invention. Further, various modifications of the invention in addition to those shown and described herein apparent to those skilled in the art from the preceding description are considered to fall within the scope of the appended claims.

Specificity of the antibodies is determined by an assay modified from the direct binding ELISA assay method of Stanker et al. (1986) (J. Immunol. 136: 4171–4180). Briefly, 96-well microtiter plates (Dynatech "Immulon-II. Alexandria, Va.) were coated with either Hb or synthetic peptide conjugated to BSA by incubating 100 $\mu$l/well of a 100 $\mu$g/ml solution of antigen for 18 hrs. at 4° C. The wells were then washed three times with phosphate-buffered saline (PBS) and nonspecific protein binding sites blocked by incubatin the plates for 1 hr. at room temperature in a 1% solution of ovalbumin (400 $\mu$l/well). After additional washes in PBS, test culture fluid or ascites fluid was added to the wells (50 $\mu$l/well), and the plates were incubated for 1 hr. at 37° C. They were then washed extensively with a detergent solution (0.05% Tween-20). Peroxidase-conjugated anti-mouse serum (U.S. Biochemicals) was then added (50 $\mu$l/well of a 1/800 dilution), and the plates were incubated for an additional 1 hr. at 37° C. Finally, 2.2 azino-di-(3-ethylbenzthiazoline sulfonic acid) substrate was added, and the enzyme activity was determined by multiple scannings by using a Titertek Multiskan 96-well microtiter plate reader (Flow Laboratories, McLean Va.). Absorbance measurements at 405 nm were recorded as a function of time and were analyzed by using computer analyses in which slopes of OD 405/hr. are calculated by using linear regression. Antibodies of this invention may be used in the form of hybridoma supernatant, or as ascites fluid or as the isolated and purified monoclonal antibodies. The sensitivity of the assay is dependent upon the type of binding antigen used to coat the microtiter plate. Any of the several described synthetic pyrethroid antigens may be used to coat the microtiter plate, including a protein conjugate of a monoester of cyclopropanedicarboxylic acid hapten of phenothrin. The compound 3-phenoxybenzoic acid (3-pba) which has been complexed with bovine serum albumin (BSA), is a preferred binding antigen.

The binding specificities of antibodies to standards and assay samples were evaluated by competition ELISA assays. In a competition assay system, an antigen, which is a large molecule with protein or carbohydrate moieties which can precisely bind with steric interaction with the conformation of the antibodies is fixed to the reaction surface of a test plate, and antigen-specific antibody is added along with an aliquot of sample extract or standard test solution. The free-floating antibody partitions between the fixed antigen bound to the test reaction surface and the antigen of the added sample or standard which is free-floating in the solution. After a reaction period, the free-floating antigen-antibody complex is washed away. The plate is rewashed and incubated with an enzyme-tagged indicator molecule which will immunospecifically bind to proteins of the animal species which was the source of the pyrethroid-specific antibodies. Substrate and buffer are provided for the reaction of the enzyme-tagged indicator molecule. The optical signal from the enzyme substrate reaction indicates the amount of pyrethroid-specific antibody which remains bound to the immobilized antigen on the reaction plate. The utility of such a reaction system is dependent on the surface binding of the antigenic hapten-protein complex. The sensitivity of such a binding system can be amplified by coupling the enzyme reaction endpoint to a biotin-avidin complex. Optimal enzyme sensitivity occurs when a minimal amount of coating antigen (3-pba-BSA) is used. The total binding capacity of the plate is large so that extra unconjugated carrier protein does not degrade binding.

The present invention also provides an improved method for identifying synthetic pyrethroids in the presence of other compounds present in food or environmental samples. The method is contemplated to be useful for the sensitive detection of synthetic pyrethroids and other pyrethroid metabolites. The specific affinity for synthetic pyrethroids of the instant monoclonal antibodies, when fixed to a binding surface, is suitable for isolation of pyrethroid metabolites from samples.

Evaluation of synthetic pyrethroid contamination of foods requires preliminary sample preparation to remove other organic material which may interfere with the sensitive antibody detection assay. Pyrethroids tend to concentrate in fat. They can be removed by rendering the fat by heating to 100° C. and extracting the pyrethroids with an organic/aqueous solvent mixture. Assay samples of food or tissue are prepared by homogenization and a preliminary extraction with a organic aqueous mixture of acetonitrile and water in the proportions of about 50–95 parts to 50–5 parts, with 85:15 being especially preferred. The fat layer is removed by chilling, and then the upper phase is extracted with hexane in a separatory funnel. Salt solution is added to improve separation of the aqueous wash layers, followed by additional distilled water washes. The hexane fraction is recovered by draining through and drying over anhydrous sodium sulfate. The pyrethroid components are removed from the hexane extracts by binding to a pretreated alumina oxide column. The pyrethroid components are eluted from the alumina column with benzene, the benzene solvent evaporated and the sample resolublized in acetonitrile. Pyrethroid content of the sample is then assayed in aqueous buffer by competition ELISA procedures.

The binding specificity for the described synthetic pyrethroids of the monoclonal antibodies of this invention may be utilized in a binding column to selectively discriminate the described synthetic pyrethroids or pyrethroid metabolites. Compounds with the 3-phenoxybenzyl and cyclopropane functionalities may reversibly bind specificly to monoclonal antibodies, produced by this invention, which are fixed in a column. Differential binding of pyrethroid compounds to a column of fixed monoclonal antibody may be used to remove, purify or concentrate these compounds. An exemplary separation method is binding and release of a compound by alteration of the ionic concentration of the column.

The following examples, presented by way of illustration, serve to explain the present invention in more detail. These examples are not to be construed as limiting the invention to the precise forms or modes disclosed. In fact, several improvements and modifications are possible. It is intended that such improvements and modifications are encompassed by the appended claims.

EXAMPLES

1. Synthesis of A Pyrethroid Hapten

The synthetic pyrethroid compound, permethrin, is a small molecule, which by itself is not immunogenic. A related hapten is formed by addition of reactive groups, which will render it immunogenic by enabling it to couple to an immunogenic carrier protein. Conjugation of carrier protein to the binding site most distant from the preferential recognition site, the 3-phenoxybenzyl group, forms a hapten which elicits an antibody which will recognize several different synthetic pyrethroids.

Figure 2:
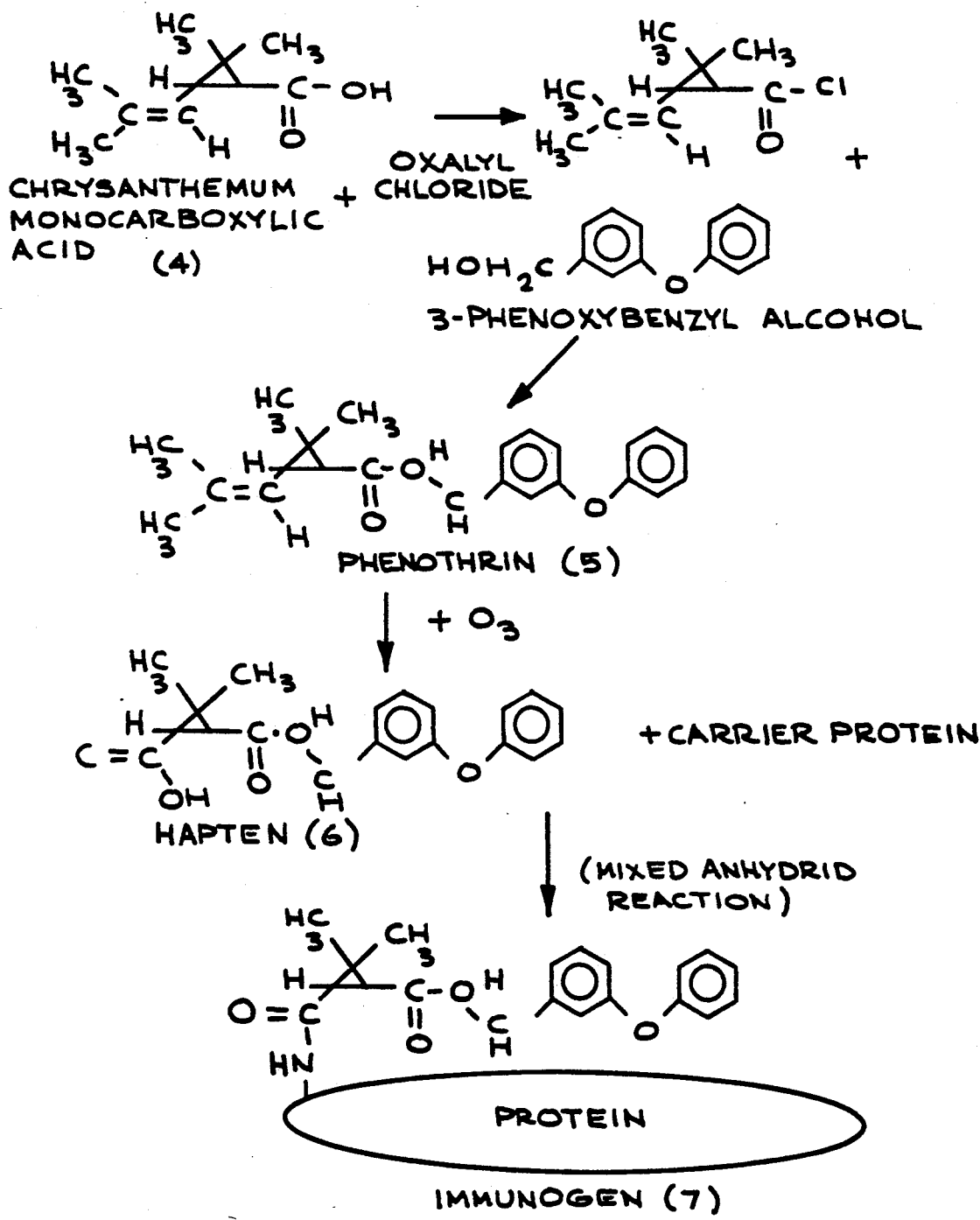
FIG. 2 presents a representative synthetic pathway for the production of the hapten-carrier protein linkage of the immunogen used to immunize mice to produce monoclonal antibodies to synthetic pyrethroids. In this example, the pyrethroid hapten was linked to the 3-phenoxybenzyl group through the carboxylic acid group. Schematically, chrysanthemum monocarboxylic acid (4) and 3-phenoxybenzyl alcohol were reacted to form phenothrin (5) which was oxidized to form the hapten, compound (6). The immunogen compound (7) was formed by linking compound (6) to KLH carrier protein.

The hapten synthesis outlined in FIG. 2 is achieved by suspending chrysanthemum monocarboxylic acid (compound 4) (1.28 g, 7.6 mM, mixed isomers) in 20 ml of methylene chloride. Oxalyl chloride (740 μl, 8.4 mM) was added followed by one drop of dimethylformamide. The mixture was stirred for 2 hours at room temperature. Then 3-phenoxybenzyl alcohol (2.00 g, 10 mM) and pyridine (2 mL) were added and the mixture stirred for an additional 12 hours. Ether was added, and the mixture was washed with saturated aqueous sodium bicarbonate, followed by water. The organic layer was dried over anhydrous sodium sulfate, evaporated, and purified by column chromatography on neutral alumina (eluted with benzene) to yield 2.2 g of phenothrin (compound 5).

A mixture of ozone and oxygen gas (3:97, w/w) (Welsbach Ozone Systems, Sunnyvale, Calif. #T-408) was passed through a solution containing 1.40 g of phenothrin (compound 5) in 200 ml of ethyl acetate (4 mM) and 10 ml of formic acid at 0° C. for 20 min at a rate of 1.2 l/min. A solution of 30% aqueous hydrogen peroxide (3.0 ml) was then added and the mixture kept at 4° C. for 12 hours. The solution was extracted twice with water and then 2M NaOH. The aqueous layer was acidified with 12 M HCl and then was extracted with methylene chloride. The organic layer was dried over anhydrous sodium sulfate and evaporated. The resulting oil was purified by column chromatogaphy on silica gel (methanol/chloroform, 3:97) to yield 360 mg (26%) of (compound 6) as an oil. The composition of the phenothrin-hapten was verified by physical analysis. FIG. 2 shows the pathway for the synthesis of the phenothrin hapten for construction of the protein-hapten conjugate used for immunization.

2. Immunization of Animals with Antigen

The hapten-protein conjugates used for immunization were produced by conjugation of the phenothrin hapten (compound 6 of FIG. 2) to keyhole limpet hemocyanin (KLH) to form (py-KLH), and to bovine serum albumin (BSA) to form (py-BSA) using the mixed anhydride method of Erlanger et al. 1959 (J. Biol. Chem. 234:1090–4). By this procedure, iso-butylchlorocarbonate is reacted with compound (6) to form an acid anhydride intermediate which readily couples to the free amine groups of the protein.

An equally useful method of conjugation of the hapten directly to the carrier protein was performed as follows: 50 mg of carrier protein was dissolved in 5 ml of double distilled water and added to 50 mg of hapten dissolved in 5 ml of water. The pH was adjusted to 7.0 by dropwise addition of dilute NaOH. Fifty mg of EDC (1-ethyl-3-(3'-dimethylaminopropyl) carbodiimide hydrochloride) was added, the mixture stirred overnight at room temperature and dialyzed for 48 hours against 4 changes of phosphate buffered saline (0.01 M phosphate, 0.155 M NaCl, pH 7.2). KLH conjugates were used for immunization and BSA conjugates were used for ELISA screening of hybridoma clones. Antibodies to pyrethroids could be raised by repeated injection of a test animal with synthetic pyrethroid-keyhole limpet hemocyanin conjugate (py-KLH). In the preferred method, the synthetic pyrethroid-keyhole limpet hemocyanin conjugate (py-KLH) was used to immunize 6-month old BALB/cBkl mice by intraperitoneal injections of 100 μg py-KLH conjugate, mixed 1:1 with complete Freund's adjuvant. The mice received a single injection every other week for three injections.

3. Production of Hybridomas

Four days prior to lymphocyte fusion, mouse hapten-specific serum titer was boosted with an intrasplenic injection of 100 μg synthetic pyrethroid-bovine serum albumin conjugate (py-BSA) in sterile saline. Hybridoma fusions, of lymphocytes to SP2/0 myeloma cells were made by standard methods( See Bigbee, W.L. et al. Molecular Immunology 20: 1353-1362 (1983)), and grown under the conditions described by Stanker et al. (1986) (J. Immunol. 136: 4174-4180) The fusion protocol was a variation of that described by Oi and Herzenberg (1981). Briefly, 4.75 ml of polyethylene glycol (PEG 1540) (Polysciences, Warrington, Pa.) was mixed with 5 ml of serum-free SDMEM, 0.75 ml of dimethylsulfoxide (DMSO) and 50 μl of 1 M NaOH. NaOH was used to bring the mixture to about pH 7.8 as judged by the phenol red in the SEMEM. The spleen lymphocytes (approximately $10^8$ cells) and approximately $10^7$ log phase myeloma cells were co-centrifuged and pelleted in a 50-ml conical centrifuge tube (Corning, Corning, N.Y.). The pellet was re-suspended in 1 ml of the 50% PEG solution over a period of 1 min. The slurry of cells was stirred for an additional minute and 2 ml of serum-free SDMEM was added over the next 2 min. followed by an additional 7 ml of serum-free SDMEM over the next 2 min. The resulting 10-ml suspension was diluted to 50 ml in SDMEM containing 2.5% RS and 1μM aminopterin. All the solutions were pre-warmed to 37° C. and maintained near that temp. during fusion with the use of a 37° C. Temp-Blok (American Scientific Products. Evanston, Ill.). The fused cells were then spread over 30 96-well microculture plates and were allowed to grow in media consisting of equal parts of M3 medium and Hanna serum-free medium (Hanna Biologicals, Berkeley, Calif.), containing 40 μM aminoptrin and 2% fetal calf serum at 37° C. in a humid 5% $CO_2$ atmosphere for 10 to 14 days before screening for antibody-producing hybridomas. Fusion is not limited to the use of SP2/0 myeloma cells and the use of other immortally reproducing cells is contemplated to be within the scope of this invention. Following fusion, hybridomas were screened in a direct binding ELISA for the ability of the antibodies which they produced to recognize the appropriate BSA-hapten conjugates.

4. Characterization of Antibodies by ELISA Assays

A direct binding ELISA was used to screen for antibodies to synthetic pyrethroids in the culture fluids of growing hybridomas. The direct binding ELISA method of Stanker et al. (1986)(J. Immunol. 136: 4174-4180) was modified as follows:

The 96-well Immulon-II microliter plates (Dynatech Laboratories, Alexandria, VA) were coated with a pyrethroid hapten-protein complex, preferably 3-phenoxy benzoic acid-bovine serum albumin complex (3-pba-BSA) in the amount of about 0.002-0.5 μg per well, preferably about 0.2 μg per well, in carbonate-bicarbonate buffer (pH 9) for 18 hours at 4° C., blocked for 1 hour at room temperature with a 1% solution of ovalbumin, and then incubated for 1 hour at 37° C. with the hybridoma supernatants. The plates were carefully washed with a solution of surfactant compounds, especially preferred was 0.05% Tween-20 TM (Polyoxethylenesorbitan Monolaurate) in water. For visualization of the binding of the pyrethroid-specific antibody from mouse, peroxidase, conjugated with goat anti-mouse antiserum, (U.S. Biochemicals, Cleveland. Ohio) diluted 1:500 in conjugate dilution buffer (0.005 M, 0.075 N NaCl, 0.001% Tween-20, pH 7.2) was added to each well. Following a second one hour incubation at 37° C., the plates were washed again and the substrate, 2,2 amino-di-3-ethylbenzthiazoline sulfonic acid (ABTS), added. Absorbance measurements at 405 nm were taken as a function of time and the resulting data were transferred to a Macintosh computer and subsequently analyzed using the "Cyberdoma" ELISA software described by Slezak et al. (1983)(J. Immunol. Methods 65: 83-95). Enzyme which participated in the color reaction was indicative of the presence of mouse antibody bound in the wells. Hybridoma cells from wells showing a positive response in the ELISA screen were expanded and subcloned twice by limiting dilution to insure their monoclonal origin. Ascites fluid was prepared in irradiated mice according to Stanker et al. (1986) (J.Immunol. Methods 136: 4174-4180) and the monoclonal antibodies purified from the ascites by hydroxylapatite chromatography (Stanker et al. (1985) J.Immunol. Methods 76: 157-169). Isotype determination was done by ELISA using mouse heavy- and light-chain specific antisera (Southern Biotechnology Assoc., Birmingham, Ala.).

Hybridomas from the fusions were cultured in 30, 96-well microculture dishes. Approximately 500 wells were observed to be secreting antibody that recognized py-BSA conjugate but not the BSA itself. Those cells showing the strongest response and specificity (approximately 250) were expanded and tested against py-BSA, py-KLH, BSA and KLH. Antibody that recognized both hapten conjugates, but not either carrier protein was observed in 29 wells. Thirteen of these were subcloned and evaluated for their ability to recognize unconjugated permethrin and cypermethrin in a competition ELISA. Antibodies from only three of the 13 hybridomas recognized the unconjugated compounds. These antibodies are named Py-1, Py-3, and Py-4.

Isotypes of the monoclonal antibodies were determined by direct-binding ELISA with isotype-specific antisera (Southern Biotech, Mobile, Ala.). All three antibodies were determined to be IgG2a antibodies with kappa light chains.

5. Competition Enzyme-linked Immunoabsorbent Assays

A competition enzyme-linked immunosorbent assay (c-ELISA) was developed to quantify permethrin standards in solution and to assess the specificity of the antibodies for various natural and synthetic pyrethroids. Any of several coating antigens could be used, however, preliminary work to optimize the sensitivity of the assay showed greatly improved sensitivity if the phenothrin-bovine serum albumin used as the synthetic pyrethroid coating antigen on the ELISA plate was replaced with 3-phenoxybenzoic acid (3-pba) conjugated to BSA. The 3-pba conjugate could be prepared by using EDC (1-ethyl-3-(3-dimethylaminopropyl)carbodiimide) as a cross-linking agent. The 3-pba conjugate was used as the coating agent for all subsequent experiments. Microtiter plates were coated with 0.5 $\mu$g/well 3-pba-BSA and blocked with ovalbumin.

In the competition ELISA, the competitors were dissolved in acetonitrile and were added to phosphate-buffered saline(PBS)-Tween buffer such that the resulting solution was 6% acetonitrile. Competitor was added so that each well contained 100 $\mu$l of competitor in a 6% acetonitrile-PBS solution. An equal volume of PBS containing monoclonal antibody was added such that there was a final concentration assay buffer containing antibody and competitor. These antibodies can tolerate up to 5% acetonitrile without loss of activity. The plates were incubated for one hour at 37° C. and the endpoint assessed by observation of the color change of p-nitrophenyl phosphate substrate actuated by alkaline phosphatase conjugated to goat anti-mouse antibody.

Because the sensitivity of c-ELISA's can be influenced by both the amount of specific anti-hapten antibody used and the amount of immobilized antigen, both of these parameters were optimized. In the preferred method, the amount of antigen used to coat the microtiter plates was varied from 10–0.5 $\mu$g/well, with 0.5 $\mu$g/well being more preferred. The method of application of the antigen to the plate was important to the assay. Antigen could be absorbed onto the wells overnight at 4° C. or antigen could be allowed to evaporate from the antigen solution onto the wells at 37° C. Using Py-1 antibody and permethrin as competitor, maximal sensitivity was observed when the antigen was allowed to evaporate onto the wells. In the preferred method microliter plates were prepared by evaporation of 100 $\mu$l of a 5 $\mu$g/mL solution of coating antigen (3-pba-BSA) at 37° C..

To detect a limited quantity of coating antigen, however, the signal must be additionally amplified. A preferred method of amplification of the enzyme-catalyzed optically-detected signal is with an avidin-peroxidase/-biotin-anti-mouse immunoglobulin system which improves the sensitivity of the immunoassay when run with low background levels of plated antigen. The avidin-peroxidase/biotin-anti-mouse immunoglobulin system may be used to improve the efficacy of enzyme-linked immunoassay as the biotin can be easily coupled to antibodies or enzymes without loss of acitivity. The exceptionally high binding affinity of avidin /M) for biotin results in the formation of bridging complexes between biotinylated molecules. Both the specific-binding monoclonal antibody and the peroxidase-enzyme indicator system are bound to biotin. Linkage of the biotin molecules with avidin results in complexing of the indicatormolecules and increased sensitive detection of the spectral signal.

Synthetic pyrethroid specific antibodies may be conjugated to biotin by methods, such as that described by P. Tijssen in Chapter 3 of "Practice and Theory of Enzyme Immunoassays" (R. H. Burdon and P. H. Vanknippenberg, Eds., Elsevier, Amsterdam (1985)). Biotinylated-N-hydroxy succinimide (BNHS) ester can be reacted with the synthetic pyrethroid-specific antibodies to make the biotinylated immunoreactants. In a preferred method, synthetic pyrethroid-specific antibody can be identified by the binding of a biotinylated anti-mouse IgG immunoglobulin to the antibody. Biotinylated peroxidase, Vectastain (Vector Laboratories, Burlingame, Calif.) can be used as the detection signal after bridging to the avidin-biotin amplification complex.

The antibody Py-1 was titrated against immobilized antigen (0.5 $\mu$g antibody/well) in a direct binding ELISA. At a Py-1 antibody concentration of 0.02 $\mu$g/well, the level used in subsequent cELISA's, 40% of the plateau activity was reached. To achieve a similar "50%" of plateau activity, antibodies Py-3 and Py-4 were used, as unpurified culture fluids, in a dilution of 1/200. A detergent, in the preferred method, Tween-20 ™, in the concentration range of about 0.0001–0.01%, preferably a concentration of 0.001%, was routinely used. Detergent concentrations greater than 0.015% interfered with the antibody activity, but if the detergent was omitted entirely, the non-specific binding activity was increased.

The competition ELISA data was normalized using 100% activity as the optical density in wells in which antibody bound to the solid phase antigen (3-pba-BSA) in the absence of any competitor. The test wells, each containing different amounts of competitor, were normalized to the 100% activity wells. Percent inhibition was calculated by subtracting the normalized percent activity from 100.

Figure 3:
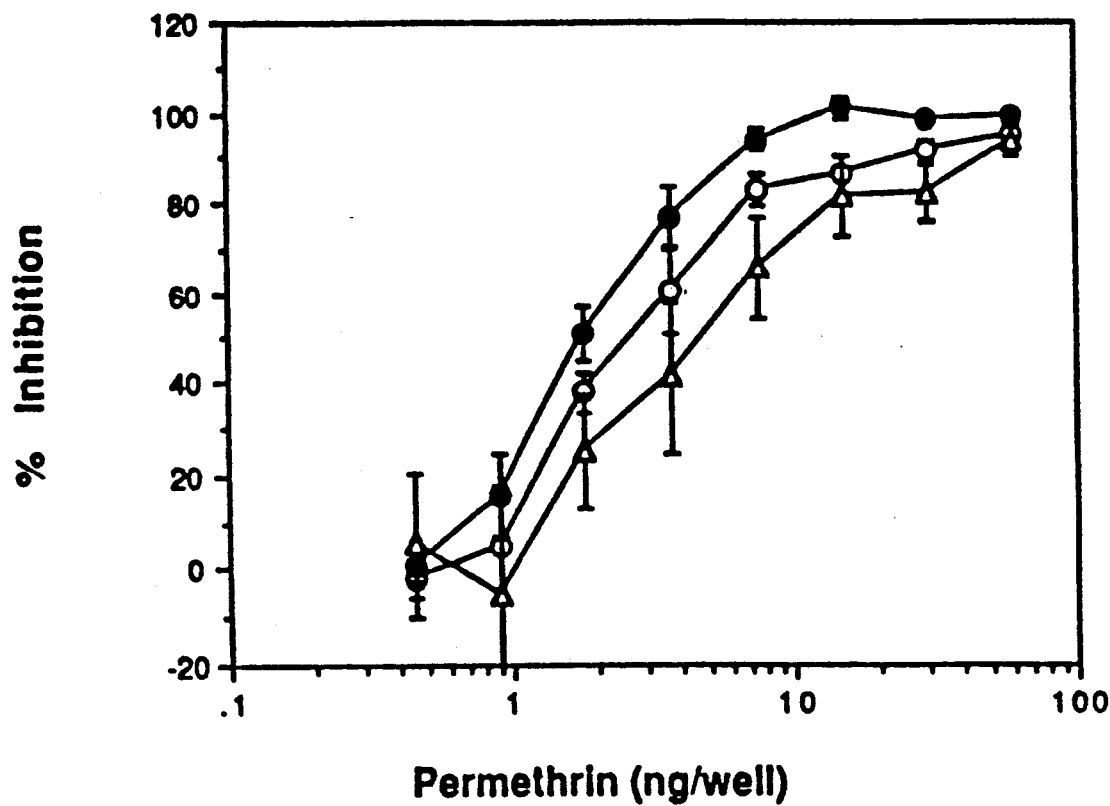
FIG. 3 shows representative competition ELISA data for the three monoclonal antibodies Py-1, (open circles); Py-3, (closed circles); and Py-4, (open triangles) when permethrin is used as a competitor. Bars represent +/− one standard deviation.

FIG. 3 shows competiton ELISA data for three monoclonal antibodies, Py-1, Py-3 and Py-4 with permethrin as the competitor (error bars represent +/− one standard deviation). The concentration of permethrin which caused a 50% inhibition ($I_{50}$) of antibody activity in the assay is in the low nanogram range for all three antibodies. The average $I_{50}$ for 49 samples of Py-1 antibody by permethrin, in assays run during a 5-month period, is 1.55 ng +/−0.6 ng.

Figure 4:
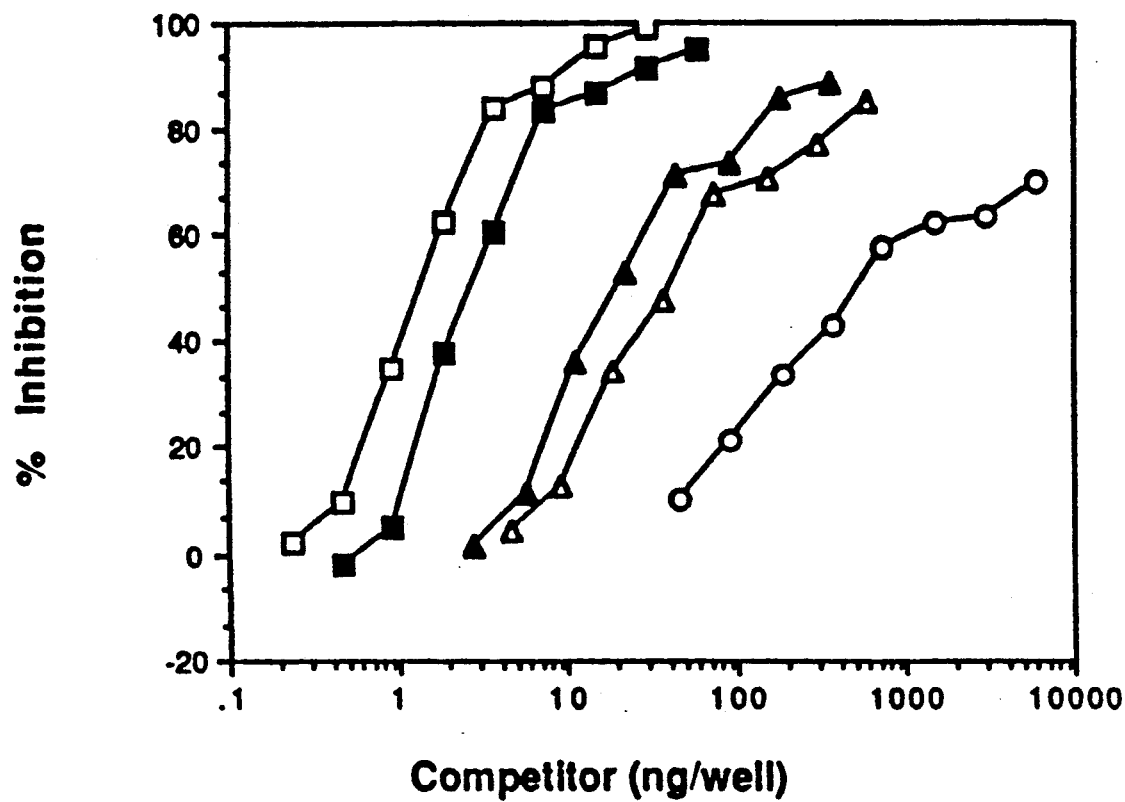
FIG. 4 shows competition ELISA data for antibody Py-1 when reacted with competitors: phenothrin, (open square); permethrin, (closed square); deltamethrin, (closed triangle); cypermethrin, (open triangle); and fenvalerate (open diamond).

FIG. 4 shows competition ELISA data for antibody Py-1 when reacted respectively with phenothrin, permethrin, deltamethrin, cypermethrin, and fenvalerate, as competitors. The $I_{50}$ values observed for these competitors were 1.5, 1.7, 15, 30 and 350 ng/well, respectively. The specificities of monoclonal antibodies Py-1, Py-3 and Py-4 are illustrated in Table 1 by the $I_{50}$ values observed with the following competitors: the hapten (compound 6 of FIG. 2), permethrin (mixed isomers), permethrin (trans isomer), 3-phenoxybenzoic acid, 3-phenoxybenzaldehyde, phenothrin, deltamethrin, fenvalerate, cypermethrin, fenpropathrin, tetramethrin, flucythranate, and chrysanthemic acid. Standard deviations of replicate assays were generally less than 0.2. The three monoclonal antibodies showed similar 50% inhibition values for permethrin, with Py-1 at 1.5 ng, Py-3 at 1.7 ng and Py-4 at 12 ng of competitor. Antibodies Py-1 and Py-3 appear to have similar reactivities, whereas antibody Py-4 is less sensitive for all competitors tested, except the hapten. A smaller $I_{50}$ value indicates a higher relative affinity of the antibody for the compound. $I_{50}$ values were estimated graphically from competition ELISA data. When 50% inhibition could not be attained, the value of the highest level of competitor tested is reported with a greater than (>) symbol. The values listed in Table 1 represent the averages from at least 12 independent assays.

TABLE I

Average[a] 50% inhibition values ($I_{50}$) in nanograms of competitors listed for Py-1, Py-3 and Py-4.

| Compound | Monoclonal Antibodies | | |
|---|---|---|---|
| | Py-1 | Py-3 | Py-4 |
| Phenothrin | 1.5 | 0.5 | 6 |
| Permethrin (mixed isomers) | 1.5 | 1.7 | 12 |
| Permethrin (trans isomers) | 1.7 | nd[b] | nd |
| Hapten[c] | 2 | 0.3 | 0.6 |
| Deltamethrin | 15 | 10 | 10 |
| Fenpropathrin | 17 | 10 | 25 |
| 3-Phenoxybenzaldehyde | 22 | nd | nd |
| Cypermethrin | 30 | 20 | 22 |
| Flucythranate | 120 | 45 | 275 |
| 3-Phenoxybenzoic acid | 200 | 140 | 330 |
| Fenvalerate | 350 | 160 | 4000 |
| Tetramethrin | >600[d] | nd | nd |
| Chrysanthemic acid | >600 | nd | nd |

[a]Averages calculated from at least 12 assays.
[b]nd = not done
[c]a monoester of cyclopropanedicarboxylic acid hapten of phenothrin
[d]50% inhibition was not observed at the highest concentration of competitor

6. Specificity of Monoclonal Antibodies in An Immunoassay in Meat Samples

To determine whether components of meats interfere with the antibody binding or immunoassay of permethrin, extracts of commercial ground beef samples were prepared by a modification of the method of Braun and Stanek, (1982) (*Assoc. Off. Anal. Chem.* 65: 685–689), and added to the assay system.

Briefly, ground beef (5 g) was mixed with 50 ml of an acetonitrile: water (85:15) solution and homogenized with a Polytron (Brinkman Instruments, Westbury, N.Y.) at setting 8 for 2 min. The sediment was removed by centri-setting fuging for 2 min at 100×G and freezing for several hours to coalesce the fat. A portion of the upper acetonitrile fraction, 8.5 ml, was mixed with 10 ml hexane in a separatory funnel (30 sec.). A solution of 2% NaCl (40 mls) was added, shaken for 1 min and allowed to stand for 2 min. The hexane fraction was extracted again with 5 ml of water (30 sec.). The hexane fraction was recovered, the funnel rinsed with an additional 5 ml of hexane and the hexane fractions pooled and dried over anhydrous sodium sulfate. The pooled hexane fraction was passed over a 1 cm pretreated alumina oxide column (AG4)(100–200 mesh) (Bio-Rad Laboratories, Richmond, Calif.), which was then rinsed with hexane. The column had previously been washed with methylene chloride for 24 hours in a Soxhlet apparatus, dried at 130° C. for 24 hours and stored at 110° C. The bound pyrethroids were released from the column with a wash of 10 ml of benzene, and the fraction was dried under a gentle stream of nitrogen. The sample was resuspended in 60 μl of acetonitrile, followed by an additional 964 ul of phosphate buffered saline (PBS) with a concentration of 0.001% Tween-20 TM. The sample was then used in a cELISA as described above.

Figure 5:
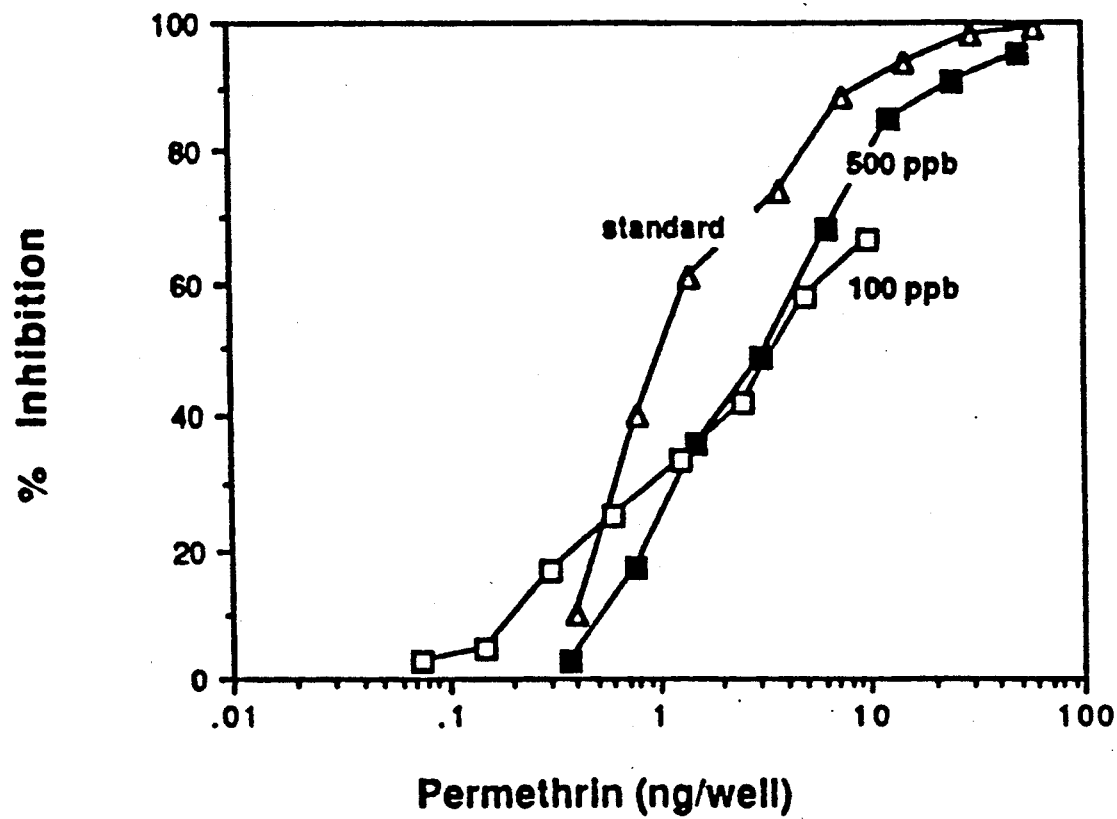
FIG. 5 shows competition ELISA data which demonstrate monoclonal antibody Py-1 detection of permethrin in meat samples. Meat samples spiked with 500 ppb of permethrin are represented by closed squares and samples spiked at 100 ppb permethrin are represented by open squares. Open triangles represent permethrin standards analyzed in sample buffer. The absolute amount of permethrin (ng/well) is plotted for the analytical standard. The spiked samples are plotted assuming 100% recovery and each well represents the extract from 0.1 g of meat.

For detection of permethrin in meats, a meat sample was extracted in an acetonitrile-water solution, partitioned against hexane, purified on an alumina column and analyzed with the cELISA method as described above. Samples were spiked with known quantities of permethrin, and cELISA curves compared with those of a standard competition curve run with permethrin in assay buffer. In FIG. 5 are depicted cELISA data of meat samples which were spiked with analytical standards of permethrin and analyzed with monoclonal antibody Py-1. Concentrations of analytical standards, 500 ppb (closed square); and 100 ppb (open square) were added to meat samples, and then extracted for assay with monoclonal antibodies. Open triangles represent permethrin standards analyzed in sample buffer. There was no competition for the antibody by unknown components in the meat when crude extract or hexane-partitioned material, spiked with permethrin, was analyzed. Addition of permethrin to the benzene extracts yielded competition curves which were similar to those observed with permethrin standards. Permethrin standards were not lost to the separation procedures of the chromatography or alumina column partitioning.

The movement of permethrin through the route of the extraction procedure in ground beef samples was further confirmed by analysis of the recovery of $^{14}$C-labeled permethrin. Analysis of spiked samples (500 ng/g of permethrin, marked with a trace amount of radiolabeled permethrin) revealed 72% +/−1.7 of the permethrin in the acetonitrile extract (after fat removal), 65.5% +/−3.5 in the hexane fraction and 62% +/−2.9 of the total radiolabel was recovered in the final benzene fraction.

7. Assay of Pyrethroids in Food Samples

Antibodies produced by the above method can be used in a testing screen to identify the presence of synthetic pyrethroids in foods in the diet. A panel of different antibodies can be used to distinguish the presence of the most commonly known pyrethroid insecticides.

Figure 6:
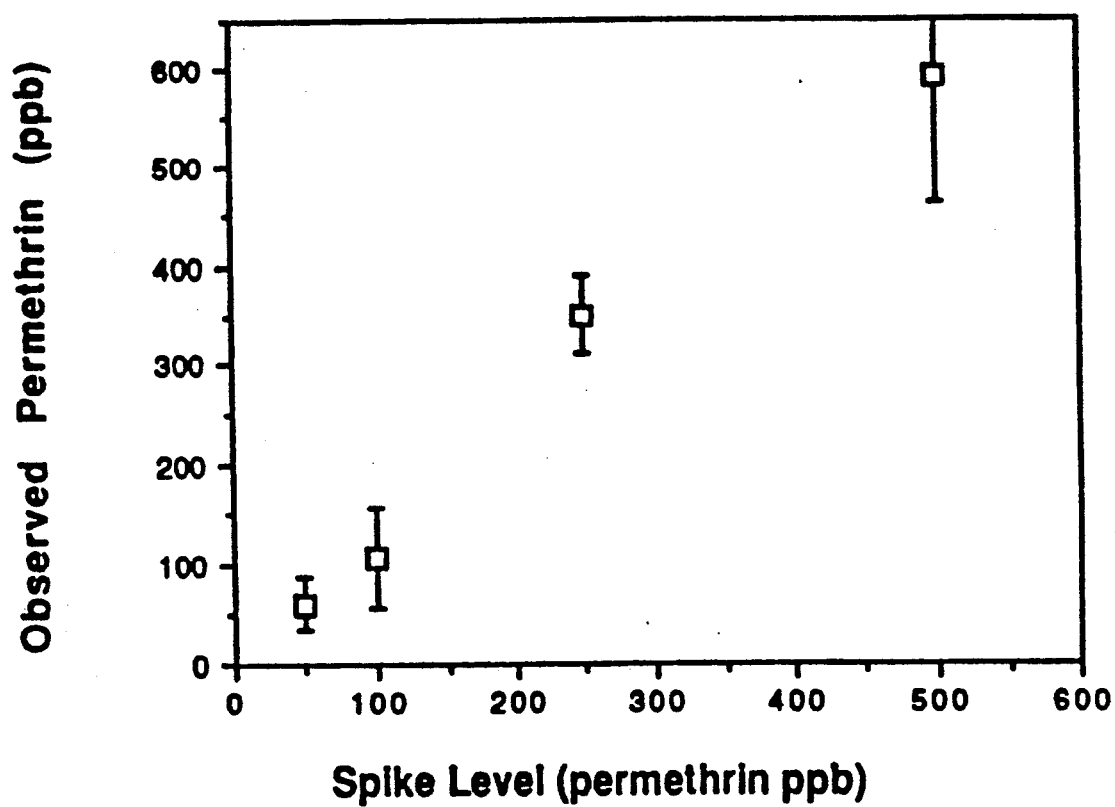
FIG. 6 shows a comparison of observed to expected permethrin analysed by competition ELISA. Permethrin contaminated ground beef samples were spiked at 500, 250, 100 and 50 ppb. Based on radiotracer studies, a 62% recovery of permethrin is assumed. Error bars represent one standard deviation from assays with at least 6 replicates per spike concentration.
Figure 2:
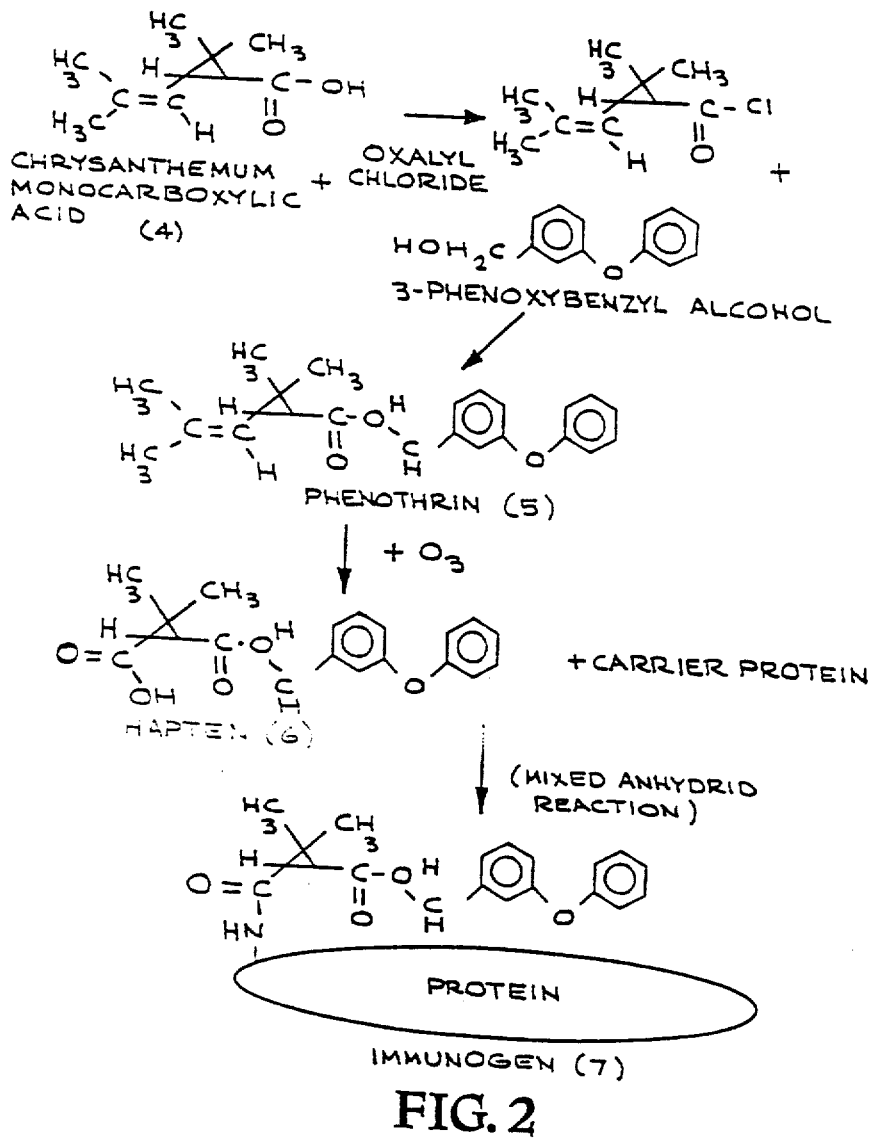

The data herein presented indicate that the antibodies developed by the described method are suitable for detection of pyrethroids in ground beef samples which have been spiked with 500 and 100 ppb of permethrin (FIG. 5). Good correlation was found between the estimated and measured levels of permethrin in all spiked samples which contained more than 50 ppb. (FIG. 6) The antibodies did not react with other constituents of meat. The expected level of permethrin contamination correlates well with that observed in spiked samples, when a 62% recovery was assumed.

The sensitivity of the assay of pyrethroids in food samples could be improved by combining the immunoassay with a preliminary HPLC separation of components of the sample. Certain retention times on HPLC could be determined and then antibodies could be used as highly selective detectors for compounds migrating at defined distances in the HPLC. The immunochemical cross-reactivity would reflect the structural similarity of synthetic pyrethroids. The combination of HPLC retention time and immunochemical detection would serve as a basis for quantifying synthetic pyrethroids. The combination of the two isolation techniques would also provide for the identification of new compounds or pyrethroid metabolites.

8. Methods for Purification of Pyrethroids

The antibodies herein developed may be covalently bound to a column and used to extract pyrethroids from samples of foods or environmental materials which are eluted through the column. Subsequent elution and repeated extraction may be used to concentrate pyrethroids and metabolites for further evaluation.

9. Kit for Field Detection of Pyrethroids

The monoclonal antibodies described herein when placed in a kit format could be used for a rapid, field portable assay for the detection of pyrethroid insecticide residues. A kit assay for field inspectors would use pyrethroid-specific antibodies including those described herein and not require use of sophisticated optical systems for detection of antibody binding reaction endpoints.

The kit would contain pyrethroid-specific monoclonal antibodies which are immobilized on the surface of a reaction vessel or plate. The immobilization surface could be on a pre-coated disposable tube or on a porous surface card, where the antibodies contact or overlay an absorbant material. Pyrethroid-specific monoclonal antibodies may be immobilized with a protein A bridge or similar protein binding complex. This binding agent would be of selected sensitivity which does not interfere with the pyrethroid binding of the specific monoclonal antibody.

The indicator enzyme-conjugated hapten, used as the reporter molecule, is selected for optimal binding to and release from the surface bound pyrethroid-specific antibody. Indicator enzyme bound to one of several antigen analogs may function to bind to and release from the surface-bound antibody, with the indicator enzyme 3-pba antigen complex, especially preferred. The enzyme-antigen conjugate may be preloaded on the antibody prior to the addition of test sample, or known standard samples, or it may be applied concurrently with the test sample. The indicator enzyme-antigen conjugate and the test sample and/or standard solutions are then allowed to compete for antibody-binding sites. In a preferred method, indicator enzyme antigen conjugate is pre-loaded. When test samples are added which contain pyrethroids, they compete with the indicator enzyme-conjugated hapten for a binding position on the immobilized antibody. Substrate is added to react with the indicator enzyme which remains bound to the immobilized antibody. Absorbance measurements are used to quantify the amount of indicator enzyme conjugate displaced by the test sample.

The kit would also provide a prepackaged sample-collecting absorbant pad, which contains organic solvent for solublization of the test sample from exposed environmental surfaces.

The above-described examples confirmed that monoclonal antibodies produced by the hybridomas designated as Py-1, Py-3, and Py-4 are highly specific to synthetic pyrethroids with the phenoxybenzyl or cyclopropane functionalities, and more particularly to those with the phenoxybenzyl and cyclopropane functionalities, and are able to distinguish compounds with similar binding activities. Binding values suggest presence of a common epitope recognized by these antibodies. The low $I_{50}$ values indicate similar degrees of recognition of permethrin, phenothrin and the hapten (compound 6 of FIG. 2) by the monoclonal antibody Py-1. The substitution of a cyano group for a hydrogen on the alpha carbon of the benzyl moiety correlates with a reduced antibody binding which is one-tenth of that for deltamethrin and cypermethrin. Selective binding of pyrethroids to this group of monoclonal antibodies indicate that these antibodies can be used to identify, simply and conveniently, low concentrations of synthetic pyrethroids present in food or environmental samples.

The subject invention thus provides monoclonal antibodies that are able to distinguish the presence of synthetic pyrethroids. The instant invention also provides cell lines which continuously secrete these monoclonal antibodies and methods for their production. The monoclonal antibodies of the subject invention bind specifically to synthetic pyrethroids and are able to distinguish compounds containing the phenoxybenzyl group and which may have the cyclopropane group. These monoclonal antibodies may be used in diagnostic applications including those where recognition of synthetic pyrethroids in the presence of other materials in foods or environmental samples is desirable. The described monoclonal antibodies are contemplated to be useful for monitoring foodstuff and environmental samples for contamination by pyrethroid insecticides.

The above embodiments were chosen and described in order to best explain the principles and the practical applications of the subject invention thereby to enable those skilled in the art to utilize the invention in various other embodiments and various modifications as are suitable for the particular use contemplated. The foregoing description of some preferred embodiments of the invention, therefore, have been presented only for purposes of description and illustration of the subject invention. It is not intended to be exhaustive or to limit the invention to the precise forms disclosed, and many modifications and variations thereof would become obvious to those skilled in the art from the teachings and disclosure herein. It is intended that the scope of the invention is best defined by the appended claims.

We claim:

1. Monoclonal antibodies which have specific affinities for compounds of the class of synthetic pyrethroids which possess the phenoxybenzyl or phenoxyphenyl functionalities, further defined in that they are secreted by hybridomas selected from the group consisting of Py1, Py-3, and Py-4, which are deposited at the ATCC with Accession Nos. HB 9996, HB 9997 and HB 9998, respectively, and said hybridomas were raised through immunization of an animal with a monoester of cyclopropane hapten of phenothrin that was conjugated to the immunogenic carrier protein through the cyclopropyl group.

2. Hybridomas, or progeny thereof, which secrete monoclonal antibodies which have specific affinities for compounds of the class of synthetic pyrethroids which possess the phenoxybenzyl or phenoxyphenyl functionalities, wherein said hybridomas are further defined in that they are selected from the group consisting of Py-1, Py-3, and Py-4, which are deposited at the ATCC with Accession Nos. HB 9996, HB 9997 and HB 9998, respectively, and wherein said hybridomas were fusions of immunoreactive cells produced by immunization of an animal with a monoester of cyclopropane hapten of phenothrin that was linked to the immunogenic carrier protein through the cyclopropyl group.

3. A method for detection of compounds of the class of synthetic pyrethroids which possess the phenoxybenzyl and cyclopropane functionalities, in samples, comprising the steps of:

extraction of said samples with acetonitrile and water to yield an organic material fraction;
extraction of said organic material fraction with hexane to remove hexane-soluble material;

attachment of said hexane-soluble material to an alumina oxide column which had been washed with methylene chloride in a Soxhlet apparatus;

extraction of said alumina oxide column with benzene solvent;

evaporation of said benzene solvent to yield a residual organic fraction;

solubilization of said residual organic fraction into aqueous solution;

addition of aqueous residual organic fraction solution to an antigen-coated reaction plate;

addition of monoclonal antibodies secreted by hybridomas selected from the group consisting of Py-1, Py-3, and Py-4, which are deposited at the ATCC with Accession Nos. HB 9996, HB 9997 and HB 9998, respectively, which have synthetic pyrethroid binding specificity;

visualization of bound synthetic pyrethroid specific monoclonal antibodies by reaction with a labeled indicator substrate which yields a detectable spectral signal.

4. A test kit for detection of synthetic pyrethroids which contain phenoxybenzyl and cyclopropane functionalities, comprising:

synthetic pyrethroid antigen immobilized on the surface of a reaction plate;

a sample solution;

enzyme-conjugated indicator; and monoclonal antibody specific for synthetic pyrethroids secreted by hybridomas selected from the group consisting of Py-1, Py-3, and Py-4, which are deposited at the ATCC with Accession Nos. HB 9996, HB 9997 and HB 9998, respectively, which partitions between immobilized antigen and antigen of solution, substrate solution which reacts with enzyme-conjugated indicator which is bound to the immobilized antibody to yield an indicator signal.

* * * * *

UNITED STATES PATENT AND TRADEMARK OFFICE
CERTIFICATE OF CORRECTION

PATENT NO. : 5,108,900
DATED : April 28, 1992
INVENTOR(S) : Stanker et al

It is certified that error appears in the above-indentified patent and that said Letters Patent is hereby corrected as shown below:

Replace Drawing Sheet 2 of 6, Figure 2 as shown with attached Figure 2.

Signed and Sealed this

Twenty-fifth Day of April, 1995

Attest:

Attesting Officer

BRUCE LEHMAN

Commissioner of Patents and Trademarks